United States Patent [19]

Henley-Cohn

[11] 4,378,806
[45] Apr. 5, 1983

[54] GAPPED RESONANT MICROWAVE APPARATUS FOR PRODUCING HYPERTHERMIA THERAPY OF TUMORS

[76] Inventor: Julian L. Henley-Cohn, 60 Lincoln St., New Haven, Conn. 06005

[21] Appl. No.: 177,388

[22] Filed: Aug. 12, 1980

[51] Int. Cl.³ .............................................. A61N 5/04
[52] U.S. Cl. ............................. 128/504; 219/10.55 F
[58] Field of Search ............... 128/804, 394, 422, 783, 128/758, 24 A; 219/10.55 F, 10.55 A, 10.55 R, 10.55 M, 10.81

[56] References Cited

U.S. PATENT DOCUMENTS

| | | | |
|---|---|---|---|
| 2,220,269 | 11/1940 | Patzold et al. | 128/804 |
| 2,242,886 | 5/1941 | Hirschland et al. | 128/804 |
| 2,407,690 | 9/1946 | Southworth | 128/804 |
| 3,077,195 | 2/1963 | Folsche | 128/804 |
| 3,095,880 | 7/1963 | Haagensen | 128/804 |
| 3,237,623 | 3/1966 | Gordon | 128/24 A |
| 3,535,482 | 10/1970 | Kluck | 219/10.55 |
| 3,668,358 | 6/1972 | Stenstrom | 219/10.65 |
| 3,800,802 | 4/1974 | Berry et al. | 128/804 |
| 3,812,315 | 5/1974 | Martin | 219/10.55 |
| 3,891,817 | 6/1975 | Brown | 219/10.55 R |
| 3,920,945 | 11/1975 | Smith | 219/10.55 R |
| 3,963,892 | 6/1976 | Camph | 219/10.55 M |
| 3,991,770 | 11/1976 | LeVeen | 128/804 |
| 4,003,383 | 1/1977 | Bruck | 128/24 A |
| 4,079,221 | 3/1978 | McGillem | 219/10.55 F |
| 4,095,602 | 6/1978 | LeVeen | 128/804 |
| 4,106,488 | 8/1978 | Gordon | 128/1 R |
| 4,108,147 | 8/1978 | Kantor | 128/804 |
| 4,119,102 | 10/1978 | LeVeen | 128/804 |
| 4,121,592 | 10/1978 | Whelley | 128/804 |
| 4,152,567 | 5/1979 | Mayfield | 219/10.55 A |
| 4,197,860 | 4/1980 | Sterzer | 128/804 |
| 4,271,848 | 6/1981 | Turner et al. | 128/804 |

FOREIGN PATENT DOCUMENTS

| | | | |
|---|---|---|---|
| 1039148 | 9/1958 | Fed. Rep. of Germany | 128/804 |
| 681690 | 1/1965 | Italy | 128/804 |
| 272419 | 3/1951 | Switzerland | 128/804 |
| 862646 | 3/1961 | United Kingdom | 128/804 |
| WO/8001462 | 7/1980 | PCT Int'l Appl. | 128/804 |

OTHER PUBLICATIONS

LeVeen et al., "Tumor Ered. by RF Therapy", JAMA, vol. 235, No. 20, p. 2198, May 1976.
Mendecki et al., "Microwave Induced . . . Treatment", J. Rad. Oncology Biol. Phys., vol. 4, pp. 1095–1103, Nov./Dec. 1978.
An RF Solution to Beef Cancer", Electronics, vol. 52, No. 11, p. 44, May 1979.
Short et al., "Physical Hyperthermic . . . ", Proceedings of the IEEE, vol. 60, No. 1, p. 133, Jan. 1980.
Brenton, "RF Used to Fight Cancer", Electronics, vol. 52, No. 9, p. 88, Apr. 1979.
"Phased Array Aids Cancer Treatment", Electronics, vol. 53, No. 27, p. 35, Dec. 1980.
Sterzer et al., "RF Therapy . . . ", IEEE Spectrum, vol. 17, No. 12, p. 32, Dec. 1980.
*Cancer Therapy by Hyperthermia and Radiation*, published 1978, Sandhu et al., "Microwave Hyper Applicators", p. 118t.
Guy et al., "Determination of Power Absorption . . . ", IEEE Trans on Biomed Eng., vol. 23, No. 5, pp. 361–371, 9/1976.
Lehmann et al., "Evaluation . . . Contact Application", Arc Phys. Med. & Rehab., 3/1970, pp. 143–146.

*Primary Examiner*—Lee S. Cohen
*Attorney, Agent, or Firm*—Pennie & Edmonds

[57] ABSTRACT

Apparatus and process for elevating the temperature of a tumor (22) by hyperthermia without unduly heating healthy tissue surrounding the tumor containing tissue, and controlling generally the temperature distribution within any dielectric medium put in place of the tissue (20), which medium acts as a dielectric load in the microwave circuit. The apparatus comprises a gapped, resonant microwave circuit having matching media for matching the intrinsic impedance of the dielectric load to the intrinsic impedance of any medium within the waveguides (16) and 16') which serve to conduct the microwave beams to the tissue (20) to be treated. Heat may be removed from the dielectric fluid (38) of a dielectric matching medium by circulating the dielectric fluid to a heat exchanger (41).

31 Claims, 5 Drawing Figures

GAPPED RESONANT MICROWAVE APPARATUS FOR PRODUCING HYPERTHERMIA THERAPY OF TUMORS

TECHNICAL FIELD

This invention relates to an apparatus for elevating the temperature of tissue by microwave irradiation, and more particularly to apparatus for treating benign and malignant tumors by microwave induced hyperthermia. Means are provided for controlling the distribution of heat within the tumor tissue.

BACKGROUND ART

Various methods and systems for producing microwave induced hyperthermia in tumors have been proposed in the prior art.

These methods, in general rely principally on the fact that a tumor, because of a slower rate of blood profusion, will be preferentially heated with respect to adjacent normal tissue when the affected area is placed in a high frequency alternating electromagnetic field.

A tumor will be necrosed when heated to a temperature of between 46° C. and 50° C. for a sufficiently long period of time. Heating to these temperatures however will severely injure normal tissue.

It has been found that in certain cases it is possible to keep the temperature of normal tissue below approximately 40° C., which results in minimal or no injury, while raising tumor tissues to high energy temperature levels to necrose the tumor.

U.S. Pat. No. 2,407,690 to Southworth discloses a microwave system for heating a liquid, or treating living tissue by applying microwave energy from a waveguide through impedance couplers, and various shapes of applicators placed in contact with the patient.

U.S. Pat. Nos. 3,991,770, 4,095,602 and 4,119,102 to LeVeen disclose systems for radio frequency heating of tissue disposed between two metallic plates connected to the output of a radio frequency generator, so that the tissue has induced within it a high frequency alternating electric field.

U.S. Pat. No. 4,121,592 to Whalley discloses microwave tissue heating apparatus utilizing tissue surface conforming metal sponges to prevent localized areas of surface tissue from overheating.

U.S. Pat. No. 3,800,802 to Berry et al. discloses an apparatus having a plurality of radio frequency magnetic induction coil heads to treat more than one patient, or different parts of the same patient simultaneously.

"Physical Hyperthermia and Cancer Therapy", by Short and Turner in *Proceedings of the IEEE*, Volume 68, No. 1 (January, 1980) provides a general summary of developments in the field of hyperthermia including reference to a system which uses "chilled distilled water ... circulated through a chamber on the front of contact applicators to draw off excess heat from the skin." (See p. 138).

While these prior art systems seemed promising, precise control of heating of tumor and healthy tissue was difficult to achieve. Often regions of healthy tissue were injured or portions of tumors left unharmed.

In addition efficient use of microwave energy would not occur because a substantial fraction of the microwave energy is subject to reflection when encountering an interface between media of substantially different electromagnetic properties, for example air and tissue, which have substantially different intrinsic impedance. This results in a lack of penetration of the microwave energy.

A further difficulty resulting from mismatch in intrinsic impedance is surface heating of the tissue. Thus skin and underlying tissue structure are subject to severe damage.

DISCLOSURE OF THE INVENTION

The present invention overcomes the abovementioned difficulties by providing an apparatus which can precisely control the location of a region of maximum heating within an area of the body that is being treated.

It also makes more efficient use of available microwave energy by effectively coupling it into the tissue. This serves to reduce undesirable surface heating and assures adequate penetration of microwave energy.

Surface heating is further reduced by a device that performs the function of coupling microwave energy as it draws off excessive heat.

The present invention provides a gapped, resonant microwave circuit in which the tissue medium to be heated, and treated by hyperthermia, is a dielectric load within the gap of such a circuit. With the proper relationship of frequency and gap dimension, standing waves can be produced within the gap, and the regions of heating optimally controlled. This is accomplished by assuring that the entire circuit, including primary resonant cavity, waveguide matching media, and the tissue form a secondary resonant circuit with a resonance at the frequency of the microwaves used.

The invention also provides a microwave matching structure to improve the coupling of microwave energy from a waveguide into tissue. Through the use of dielectric layers of increasing intrinsic impedance, preferably including dielectric fluid-filled plastic bags at the tissue interface, the microwave energy is efficiently coupled into the tissue. The use of fluid-filled plastic bags is advantageous in that the bag contents conform to the irregular shape of the surface of the tissue, to prevent overheating of local areas which could not be maintained in uniform coupling contact with a solid matching medium.

The dielectric fluid-filled bags afford the additional advantage that the dielectric may be circulated to a heat exchanger to remove heat and thus aid in preventing the surface tissue or skin from being heated to excess.

BRIEF DESCRIPTION OF THE DRAWINGS

Further objects and advantages of the invention may be readily ascertained by reference to the following description and appended drawings, which are offered by way of description only and not in limitation of the invention, the scope of which is defined in the appended claims.

BEST MODE FOR CARRYING OUT THE INVENTION

Figure 1:
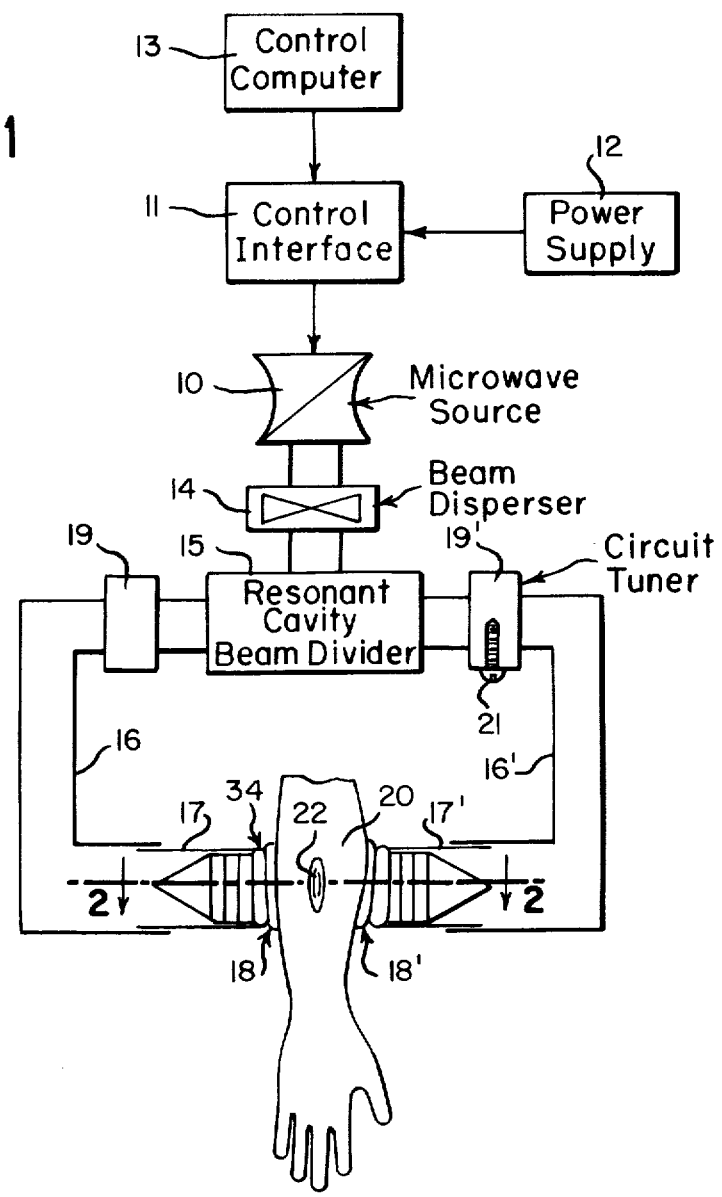
FIG. 1 is a block diagram of a microwave therapy system according to the invention.

Referring to FIG. 1, a microwave source 10, preferably a klystron or a magnetron, provides microwave energy in the general frequency range of about 100 MHz to 2.5 GHz, either pulsed or continuous. The output of source 10 may be controlled in time, amplitude, or frequency or in any combination of these or other relevant parameters by control interface 11 which controls the application of power from power supply 12 to the microwave source 10 as directed by the outputs of a control computer 13. Control computer 13 is preferably a digital computer designed or programmed to analyze input commands and dose data from various sensors, compute the necessary control outputs used by the control interface 11, and possibly store data on relevant parameters.

The microwave source 10 is coupled to a beam disperser 14, of the kind well known in the microwave art. Beam disperser 14 produces a uniform spartial microwave energy distribution within the primary resonant space.

The output of either beam disperser 14 or source 10 (if beam disperser 14 is not used) is connected to divider 15 which serves to divide the microwave energy into two microwave beams of approximately equal intensity. Such dividers are well known in the microwave art and may comprise simply a cavity resonant at approximately the frequency of the microwave source with ports on two opposite sides. This resonant space or cavity thus is a primary resonant source of microwave energy for the secondary resonant circuit mentioned above, and more fully described below. The resonant microwave circuit is thereby coupled to the primary space by various means described below.

Connected to the divider 15 are two waveguides 16 and 16' which serve to conduct the microwave beams from the divider 15 to the tissue 20 to be treated. These waveguides 16 and 16' are generally of the type well known in the microwave art. At higher frequencies such as 2000 MHz the TE or TM modes of propagation may be used. Lower frequencies would require the use of fairly large, cumbersome waveguides to assure that the waveguide cut-off frequency is below the frequency of the microwaves used. The cross section of the waveguides 16 and 16' can be reduced in size by filling the waveguide with a dielectric material, such as a fluid, or a solid, perhaps in powdered form which does not unduly absorb the microwave energy. This technique also provides the advantage of allowing smaller volumes of tissue 20 to be treated at any given frequency.

The waveguides 16 and 16' may be of the flexible variety to allow for positioning to form a variable gap in which the medium or tissue 20 may be disposed. Waveguides 16 and 16' may be partially flexible and partially rigid or entirely rigid having telescoping sections 17 and 17' to allow for adjusting both the dimension of the gap in the direction of wave propagation and the phase of the microwave energy which is conducted to the matching media 18 and 18', which serve to aid in coupling the microwave energy into the tissue 20. The matching media are more fully described below. Telescoping sections 17 and 17' are aligned on a common axis.

Situated along the waveguides 16 and 16' are circuit tuners 19 and 19'. Tuners 19 and 19' are advantageously resonant cavities which serve several functions. If a microwave source 10 which produces a variety of frequencies is used, tuners 19 and 19' can be used to greatly attenuate all but the desired frequency. The importance of using single frequency radiation in certain cases will become apparent following the discussion below, in Example I. In addition if telescoping sections 17 and 17' are not provided, adjustment of the relative phase of the radiation at the matching media 18 and 18' can be accomplished by use of circuit tuners 19 and 19'. Also the desired phase adjustment can be accomplished if the circuit tuners 19 and 19' are adapted to receive various dielectric or conductive shapes 21, which can be positioned within the circuit tuners 19 and 19' as shown. Such phase adjustment is necessary to tune the microwave circuit to resonance as discussed below.

As will become apparent to one skilled in the art, a standing wave of microwave energy is generated in the gap between the two matching media 18 and 18' and may comprise multiple half wavelengths or a single half wavelength.

If any dielectric medium, or in particular a section of tissue 20, is inserted in the gap, the effective dielectric constant for an integral number of half wavelengths will change, due to the fact that the microwave energy has a different wavelength in that medium. It then will be necessary to tune the microwave source 10 to a different frequency to establish an integral number of half wavelengths in a particular gap dimension. Tuning can also be achieved by fine control of gap space adjustment.

A major advantage of using the configuration of FIG. 1 is that a resonant microwave circuit or loop has been formed in which the dielectric medium to be heated is a dielectric load. Thus, instead of being irradiated from the outside, the tissue 20 and tumor 22 are part of the microwave circuit comprising the beam divider 15, the waveguides 16 and 16', telescoping sections 17 and 17', the circuit tuners 19 and 19', and the matching apparatus which will be more fully described below. This microwave circuit has a total effective path length such that it is resonant at the frequency of the microwave source used. Proper selection and adjustment of parameters allows for precise control of which regions within the dielectric medium or tissue 20 are heated to a greater or lesser extent. To accomplish precise control it is necessary that only one frequency component with substantial amplitude be present, or that any frequency components present are at a frequency which corresponds to a resonance of the microwave circuit, and are preferably harmonics of the frequency of substantial amplitude.

EXAMPLE I

The frequency of the microwave source 10, can be selected so that the gap dimension is an effective half wavelength of the microwave radiation in the tissue. The term effective half wavelength is used to broadly encompass any path length through the tissue 20 which provides a time delay of one half the period corresponding to the frequency of the microwave energy produced by the microwave source 10. Suitable manipulation of the telescoping sections 17 and 17' of the waveguides 16 and 16' while keeping the matching media 18 and 18' in contact with the tissue, will provide a means for varying the region within the tissue where constructive interference, or a loop, in the standing wave pattern results. This region is thus preferentially heated. A tumor 22 located in such a region will be heated to a greater extent than the tissue 20 comprising healthy tissue surrounding the tumor. Since tumor or unhealthy tissue is less tolerant to heating than healthy tissue, this fact can be exploited to a greater extent by preferential heating of the unhealthy tissue of tumor tissue 22 without an adverse effect on tissue 20 surrounding the tumor.

To further aid in preferential heating of unhealthy tissue, while minimizing the heating of healthy tissue, it is possible to use more than one pair of waveguides 16 and 16' with a gap volume common to all pairs of waveguides. The simplest case would require four waveguides attached to microwave divider 15, the additional two waveguides being connected to ports on the remaining two opposite unused sides of the divider 15, and configured in the same fashion as waveguides 16 and 16', resulting in the gap between matching media 18 and 18' being irradiated by two beams crossing at the center of the gap, but traveling in directions ninety degrees apart.

Many other configurations using more than one pair of waveguides can be envisioned, including the use of multiple, synchronized sources to energize the waveguides without departing from the scope of the invention.

It will become apparent to those skilled in the art that it would be desirable to assure that the distribution of heating which will occur inside tissue is the distribution sought. This can be verified by making up an appropriate dielectric model of the tissue with numerous temperature measuring devices located within it. Such models are well known in the microwave therapy art. The temperature that these devices indicate on appropriate readout means can be monitored, and the data obtained can be used to properly adjust various parameters to obtain the proper results. Then the patient may be inserted for therapeutic purposes without any risk of excessive heating in areas where it is not desired.

EXAMPLE II

The frequency of the microwave source 10, can be chosen to be rather high, so that a large number of half wavelengths fall within the gap between the matching media 18 and 18'. In this case, substantially uniform heating of tissue 20 in the gap will occur. This approach is most useful if a tumor occupies almost the entire volume of tissue exposed to microwaves or if the dielectric medium is a solution to be heated so as to sterilize it. In this use it would not be necessary that only one frequency component with substantial amplitude be present.

While the apparatus outlined in FIG. 1 solves a multitude of practical problems associated with microwave induced hyperthermia therapy, it is still often the case that healthy tissue, especially surface tissue, is heated to excess because of reflections due to the difference in intrinsic impedance between the medium within the waveguide which is usually air, and the impedance of the dielectric medium, which in the case of tissue is very often approximately that of water.

The intrinsic impedance of any medium is defined as the square root of the quotient of the permitivity over the permeability of that medium. If two media have substantially equal intrinsic impedance, then microwave energy is transmitted easily from one medium to the other and only a small amount of energy is reflected. If the media have drastically different intrinsic impedances, microwave energy traveling within one medium is virtually all reflected at the interface with a second medium, and only a small amount enters the second medium.

If the media through which microwave energy is propagated are all essentially nonmagnetic in nature, then the permeability of these media will be essentially equal to that of vacuum or air. In such a case the extent of the reflection of microwave energy can be determined by comparing the permittivity of the media or their dielectric constants, without the need to consider impedance. This is often the case when microwave energy is coupled from air to tissue.

Figure 2:
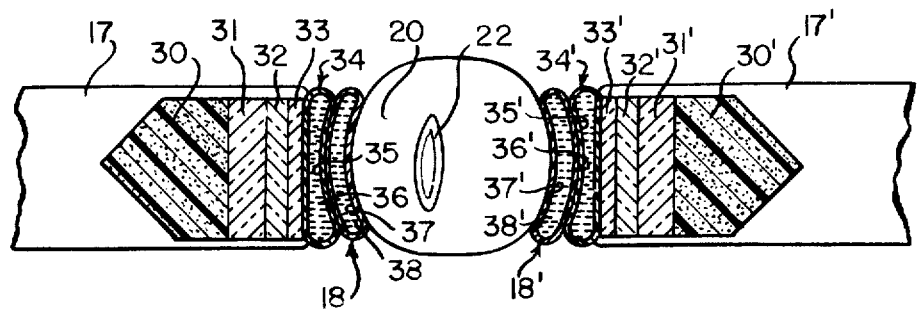
FIG. 2 is a cross section of parts of the waveguide and an impedance matching apparatus taken along the section line 2—2 of FIG. 1.

Referring to FIG. 2, microwave energy travels along the telescoping sections 17 and 17' of the waveguides 16 and 16', or if telescoping sections 17 and 17' are not provided, to the end of the waveguides 16 and 16' where it encounters several layers of dielectric media 30, 31, 32, 33, 34 and 18 associated with end of telescoping section 17 and 30', 31', 32', 33', 34' and 18' associated with the end of telescoping section 17'. Discussion will be restricted to the layers of dielectric media associated with the end of telescoping section 17 although it is also applicable to the layers of dielectric media associated with the end of telescoping section 17'.

For optimum transfer of energy the layers of dielectric media 30, 31, 32, 33, 34 and 18 are chosen to have gradually increasing intrinsic impedance (or equivalently for nonmagnetic materials, increasing dielectric constants). Thus, the medium 30 adjacent to the medium within the end of telescoping section 17, will have an impedance higher than that of the medium within the waveguide 16 and telescoping section 17, and the matching medium 18 will have an intrinsic impedance lower than or equal to that of the medium or tissue 20 to be irradiated. These dielectric media may have an intrinsic impedance approximately equal to the geometric mean of the intrinsic impedance of the medium disposed on either side of that matching medium and should have a dimension in the direction of propagation of the microwave energy equal to a multiple of a half wavelength of the microwave energy within that medium, preferably one half wavelength.

In order to achieve the proper dielectric constants and therefore the proper intrinsic impedance some of the matching media may be nonmetallic bags filled with dielectric fluid. A further advantage of using a fluid-filled matching medium 18 in FIG. 2 is apparent. The fluid-filled matching medium 18 will conform to the shape of tissue 20 which is to be heated. This will further serve to prevent areas of tissue 20 from becoming overheated due to contact or lack of contact of the matching medium 18 immediately adjacent to tissue 20, and the tissue 20.

If the matching medium 18 is used as a conforming layer, it may not be possible for it to be held to exactly one half wavelength along the direction held to exactly one half wavelength along the direction of microwave propagation, because it will change thickness as needed to conform to the dielectric medium or tissue 20, which is being heated.

This problem can be overcome by choosing the impedance of the dielectric medium to be approximately equal to that of the medium or tissue 20 to be heated. Then the fluid-filled dielectric medium 18 becomes, from a microwave standpoint, an extension of the tissue 20 and only minimal heating of the surface of the tissue 20 can occur.

A preferred embodiment of the microwave impedance matching device illustrated in FIG. 2 is set out below. It is designed to match microwave energy of 2450 MHz traveling within an air-filled waveguide of rectangular cross section 7.2 cm×3.4 cm to tissue of dielectric constant of approximately 80.

EXAMPLE III

The matching medium 30 may be composed of a methyl methacrylate polymer within which is dispersed carbon or ferrite particles such medium having a dielectric constant of 2.63. As is often the case for microwave terminating devices, the matching medium 30 may have a cone or wedge shape to aid in extracting energy from the end of telescoping section 17 of the waveguide 16, by helping to reduce reflections back into the end which may be filled with air having a dielectric constant of approximately 1.00.

Matching medium 31 may be composed of Vycor glass type 7910 or 7911 having a dielectric constant of 3.8, and a dimension, or thickness, in the direction of propagation of the microwave energy, of 3.2 cm.

Matching medium 32 may be composed of Corning ® glass type 0010 having a dielectric constant of 6.3 and a thickness of 2.4 cm.

Matching medium 33 may be composed of Corning ® glass type 8870 having a dielectric constant of 9.5 and a thickness of 2.0 cm.

The above-mentioned glasses are of proprietary compositions, but are well known in the radar art. The dielectric constants are produced by the introduction of silicon, carbon, or lead into various glasses. Some properties of these glasses are set out in the Handbook of Physics and Chemistry, published by The Chemical Rubber Company, 55th ed. (1974-75) at page E-60.

Matching medium 34 may be a plastic bag 35 filled with propanol 36, having a dielectric constant of 22.9.

Matching medium 18 may also be a plastic bag 37 which contains a dielectric fluid 38. The dielectric fluid may be glycerol having a dielectric constant of 42.5 or ethylene glycol having a dielectric constant of 37.0 or a mixture of glycerol and water having a dielectric constant which can be adjusted by varying the relative proportions of glycerol and water.

As an alternative, as discussed above, it is possible for the dielectric fluid 38 in matching medium 18 to be almost pure water which, as is the case for many tissues, has a dielectric constant of approximately 80 so as to approximate the intrinsic impedance of the tissue 20. The intrinsic impedance of the dielectric fluid 36 in matching medium 34 may then be chosen to have an intrinsic impedance between that of matching medium 33 and matching medium 18, and matching medium 33 may be constrained by suitable means to be approximately one half wavelength in dimension in the direction of the propagation of microwave energy. In this case matching medium 18 may be a rather thin layer or pad, so as to not unduly absorb energy.

Note that several of the matching media 30, 31, 32 and 33 are disposed within the end of telescoping section 17 of the waveguide. This helps to reduce microwave radiation in directions other than in the direction toward the tissue 20 to be heated. It has been found unnecessary to place matching media 34 and 18 within the end of the telescoping section of the waveguide to avoid strong radiation because microwaves will not radiate outwards from media of high permittivity, but all of matching media 34, and even a portion of the thickness of matching medium 18 are preferably placed within the end of the telescoping section 17 of the waveguide 16.

As described above, it is possible to propagate a given frequency in a waveguide of smaller cross section as the dielectric constant of the medium within the waveguide is increased. It is thus possible to use successively smaller, or tapered matching media, to decrease the area of heating, for the treatment of small tumors, while employing the same waveguide.

Figure 3:
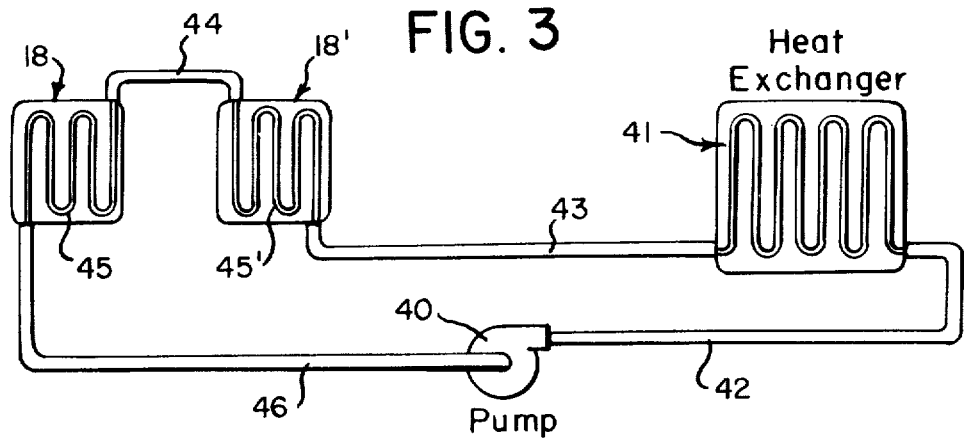
FIG. 3 is a schematic diagram of a cooling apparatus for the applicator section of the impedance matching apparatus illustrated in FIG. 2.

FIG. 3 illustrates a means for further assuring that the surface of tissue treated by microwave induced hyperthermia is not damaged by excessive heating. Dielectric fluid used in the matching media 18 and 18' may be circulated to a heat exchanger 41, where heat is removed. A pump 40, serves to circulate the fluid, by means of tubes 42, 43, 44, 45, 45' and 46 through the matching media 18 and 18'.

The fluid circulated can be a different fluid, if desired, which has similar dielectric properties to those of dielectric fluid 38 contained in the plastic bag 37, and would be physically isolated from the dielectric fluid 38 by means of plastic heat exchanging tubes 45 and 45' located within matching media 18 and 18'.

Figure 4:
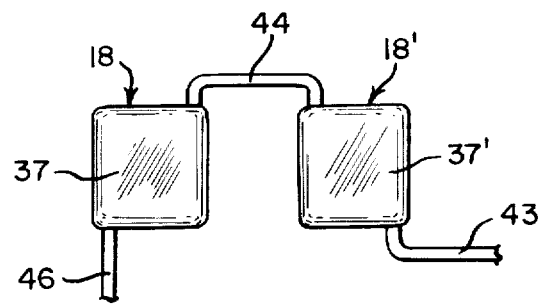
FIG. 4 is an alternate embodiment of the applicator section of the apparatus illustrated in FIG. 3.

Alternatively, FIG. 4 illustrates an embodiment of matching media 18 and 18' in which the fluid circulated may be the same fluid as is used in the matching media, and would therefore be simply circulated into and out of the plastic bags 37 and 37'. In this case, the plastic heat exchanging tubes 45 and 45' would not be used. Relative costs of the dielectric fluids may determine which of the above approaches would be used.

The structure of FIG. 2 is somewhat complex and there is occasional difficulty in obtaining dielectric glass plates of the proper thickness from the supplier when they are required.

Figure 5:
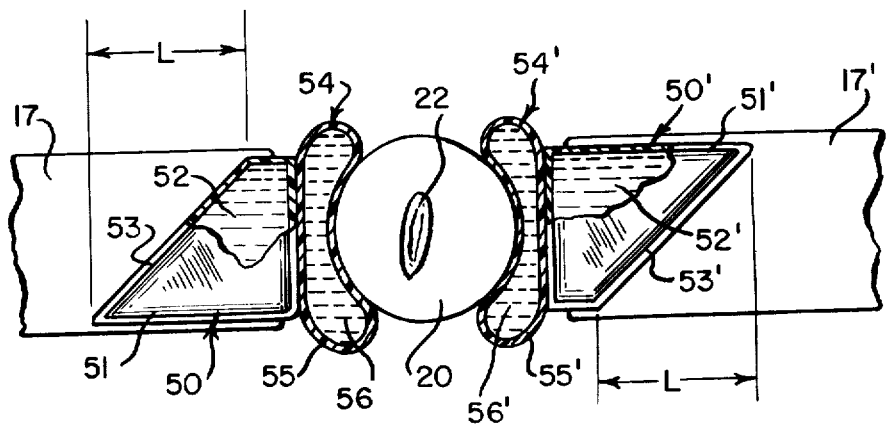
FIG. 5 is an alternate impedance matching structure which can be used in place of the structure shown in FIG. 2. In the drawings and the following descriptions, like portions or parts are denoted by like numerals or characters.

FIG. 5 illustrates an alternate structure for a microwave matching apparatus which may be used in the invention. It is comprised of dielectric media 54 and 54' and matching sections 50 and 50' having a wedge shape located within telescoping sections 17 and 17'. These matching sections may be formed from a solid dielectric material, or may be, as shown, comprised of a rigid, nonmetallic shell 51 and 51' within which is contained a dielectric fluid 52 and 52' or possibly a dielectric powder. The dielectric constant of matching sections 50 and 50' should be in the range of 50 to 80, being approximately equal to that of the tissue 20, or slightly lower. Matching sections 50 and 50', if formed from solid dielectric material, may be advantageously comprised of a ceramic loaded with titanium dioxide. If a dielectric fluid is used it may be glycerol, or a mixture of fluids, such as glycerol and water, which has a dielectric constant approximately equal to that of the tissue 20, or dielectric media 54 and 54' (more fully described below), or some value in the range between them.

The length of the sloping or wedge section of matching sections 50 and 50' along the direction of propagation of microwave energy is shown by the length L in FIG. 5. The length L, should be equal to at least two wavelengths of the microwave energy within telescoping sections 17 and 17' of waveguides 16 and 16'. This allows microwave energy traveling in telescoping sections 17 and 17' to be exposed to a gradually increasing dielectric loading as the cross section of telescoping sections 17 and 17' becomes increasingly dominated by matching sections 50 and 50'. Thus the average impedance which any unit of space through which the microwave energy propagates gradually increases, resulting in minimized reflection of microwave energy.

Matching sections 50 and 50' are disposed within the telescoping sections 17 and 17' so that their sloping surfaces 53 and 53' are parallel to one another. This results in the entire cross section of the microwave energy traveling through the same distance of the medium of matching sections 50 and 50'. Thus, any attenuation which might tend to produce a nonuniform beam is uniform throughout the cross section of the waveguide.

Dielectric matching media 54 and 54' perform essentially the same function as dielectric matching media 18 and 18' of FIG. 2. These media are comprised of a nonmetallic enclosure or bag 55 and 55' which contain a dielectric fluid 56 and 56'. The dielectric constant of this fluid is chosen to be in the range of 50 to 80, and is preferably that of, or just below that of, the tissue 20 within which the tumor 22 which is to be treated in located. A mixture of glyercol and water can be adjusted in composition to provide the desired dielectric constant and hence the proper impedance.

As in the case of dielectric matching media 18 and 18' of FIG. 2, the cooling arrangements of FIG. 3 or FIG. 4 may be used to cool the dielectric matching media 54 and 54'.

It will become apparent to one skilled in the microwave art that while the invention described herein is intended to be used primarily for therapeutic purposes, it may have application in a variety of industrial processes where it is desirable to increase the temperature of a localized area within a dielectric medium. If surface heating is desired, the dielectric matching media may be omitted.

Various modifications of the invention in addition to those shown and described herein will become apparent to those skilled in the art from the foregoing description and accompanying drawings. Such modifications are intended to fall within the scope of the appended claims.

I claim:

1. An apparatus for treating biological tissue by microwave induced hyperthermia comprising:
    (a) a primary resonant source of microwave energy,
    (b) a resonant microwave circuit including a pair of resonant waveguide means coupled to said primary resonant source to form a resonant loop having a gap between spaced ends of said waveguide means, and wherein a dielectric loading comprising the biological tissue to be treated is adapted to be located within said gap, and
    (c) layered dielectric means at each of said spaced ends providing an interface between said tissue and said waveguide means for optimally coupling said microwave energy in opposite directions, said layered dielectric means including a plurality of dielectric media with each dielectric medium providing a gradual increase in intrinsic impedance in the direction of propagation of said microwave energy.

2. An apparatus for treating biological tissue by microwave induced hyperthermia comprising:
    (a) a primary resonant source of microwave energy,
    (b) a resonant microwave circuit including a pair of resonant waveguide means coupled to said primary resonant source to form a resonant loop having a gap between spaced ends of said waveguide means, and the biological tissue to be treated comprising the dielectric loading adapted to be located within said gap, and
    (c) means interposed between said dielectric loading and each of the spaced ends of waveguide means interfacing said waveguide means and said tissue for optimally coupling said microwave energy of said microwave circuit in opposite directions, said coupling means including
        (1) a wedge-shaped dielectric medium in contact with a medium having an intrinsic impedance and
        (2) a dielectric fluid-filled nonmetallic enclosure in contact with both said wedge-shaped dielectric medium and a medium of higher intrinsic impedance.

3. The apparatus of claims 1 or 2 wherein said primary resonant source produces a standing wave within said gap.

4. The apparatus of claim 3 wherein the frequency of the microwave energy and the dimension of said gap produces a standing wave within said gap in the direction of propagation of the microwave energy which is an effective integral number of half wavelengths of the microwave energy.

5. The apparatus of claim 4 further comprising a circuit tuner located along each said waveguide means to tune said source of microwave energy to maintain said standing wave when said dielectric loading has a dielectric constant different than the dielectric constant across said gap.

6. The apparatus of claim 3 wherein the frequency of the microwave energy and the dimension of said gap produces a standing wave within said gap in the direction of propagation of the microwave energy which is an effective half wavelength of the microwave energy.

7. The apparatus of claim 6 further comprising a circuit tuner located along each said waveguide means to tune said source of microwave energy to maintain said standing wave when said dielectric loading has a dielectric constant different than the dielectric constant across said gap.

8. The apparatus of claims 1 or 2 further comprising a circuit tuner located along each said waveguide means.

9. The apparatus of claims 1 or 2 wherein the waveguide means are filled with a dielectric material.

10. The apparatus of claims 1 or 2 further comprising means for adjusting the width of said gap between the spaced ends of said waveguide means which are in proximity with the tissue to be heated so as to form a gap equal to an effective integral number of half wave lengths in the direction of propagation of the microwave energy.

11. The apparatus of claims 1 or 2 including means for adjusting the length of said waveguide means to change the phase of the outputs of said waveguide means.

12. The apparatus of claim 1 further comprising nonmetallic exclosure juxtaposed each end of said waveguide means forming at least the dielectric medium juxtaposed said tissue, a dielectric fluid displaying an impedance matching capability and serving to reduce the surface heating of tissue exposed to said microwave energy, said nonmetallic enclosure defining the volume of said dielectric fluid juxtaposed said tissue and adapted to conform the dielectric fluid to substantially any irregularities of the surface.

13. The apparatus of claim 12 further comprising:

(a) a heat exchanger, and (b) means for circulating said dielectric fluid to said heat exchanger in order to cool said dielectric fluid.

14. The apparatus of claims 12 or 13 wherein the dielectric fluid is glycerol.

15. The apparatus of claims 12 or 2 wherein the dielectric fluid is propanol.

16. The apparatus of claims 12 or 2 wherein the dielectric fluid is ethylene glycol.

17. The apparatus of claims 12 or 2 wherein the dielectric fluid in said nonmetallic enclosure is a mixture of water and glycerol, and wherein the proportions of said mixture of water and glycerol for providing optimum impedance match may vary from a mixture of almost pure water to a mixture having a lesser amount of water.

18. The apparatus of claim 1 wherein said layered dielectric media is disposed in contact with one another, each such layered dielectric medium having an intrinsic impedance greater than the preceding layered dielectric medium, the layered dielectric medium of lowest intrinsic impedance being in contact with a medium having an intrinsic impedance lower than the intrinsic impedance of said contacting dielectric layer, and the layered dielectric medium of highest intrinsic impedance being in contact with a medium of higher intrinsic impedance and having an intrinsic impedance not more than equal to that of the medium of higher intrinsic impedance.

19. The apparatus of claim 18 in which the layered dielectric media, in the direction of propagation of said microwave energy, comprise:

(a) methyl methacrylate polymer containing carbon particle;
(b) Vycor glass 7910;
(c) Corning ® glass 0010;
(d) Corning ® glass 8870;
(e) a plastic bag filled with propanol;
(f) a plastic bag filled with a mixture of glycerol and water; and
(g) a plastic bag filled with a mixture of ethylene glycol and water.

20. The apparatus of claim 18 wherein the layered dielectric medium of highest intrinsic impedance comprises a plastic bag filled with ethylene glycol.

21. The apparatus of claim 23 wherein each layered dielectric medium which is located between two other layered dielectric media is chosen to have an intrinsic impedance within the range between the intrinsic impedance of the two layered dielectric media on either side of such layered dielectric medium.

22. The apparatus of claim 24 wherein the two layered dielectric media of highest intrinsic impedance comprise:

(a) a plastic bag filled with propanol, and
(b) a plastic bag filled with glycerol, the plastic bag filled with glycerol being in contact with the medium of high intrinsic impedance.

23. The apparatus of claim 18 wherein the layered dielectric medium of highest intrinsic impedance comprise:

(a) a dielectric fluid, and
(b) an enclosure which defines a volume of said dielectric fluid adapted to conform to the irregularities of a surface of the medium of high intrinsic impedance with which it is in contact.

24. The apparatus of claim 2 wherein the dielectric fluid-filled nonmetallic enclosure is a plastic bag.

25. The apparatus of claim 2 wherein the wedge-shaped dielectric medium is comprised of a solid.

26. The apparatus of claim 2 wherein the wedge-shaped dielectric medium has a dielectric constant in the range of 50 to 80.

27. The apparatus of claim 2 wherein the wedge-shaped dielectric medium is comprised of a nonmetallic enclosure defining a volume of dielectric fluid.

28. The apparatus of claim 2 wherein the wedge-shaped dielectric medium is comprised of a nonmetallic enclosure defining a volume of dielectric powder.

29. The apparatus of claim 2 wherein the length of the sloping section of the wedge-shaped dielectric medium in the direction of propagation of the microwave energy is at least two wavelengths.

30. The apparatus of claim 2 wherein the sloping sides of each wedge-shaped dielectric medium is disposed so that the sloping sides are generally parallel to one another.

31. The apparatus of claim 2 further comprising:

(a) a heat exchanger, and
(b) means for circulating dielectric fluid from said enclosure to said heat exchanger to cool said dielectric fluid and the tissue in said gap.

* * * * *